United States Patent [19]

Katayanagi et al.

[11] Patent Number: 4,760,748
[45] Date of Patent: Aug. 2, 1988

[54] OPTICAL DETERIORATION-ACCELERATING WEATHER AND OPTICAL RESISTANCE TESTING APPARATUS

[75] Inventors: Shinichi Katayanagi; Taro Mori, both of Tokyo, Japan

[73] Assignee: Suga Test Instruments Co., Ltd., Tokyo, Japan

[21] Appl. No.: 948,061

[22] Filed: Dec. 30, 1986

[30] Foreign Application Priority Data

Apr. 7, 1986 [JP] Japan ................................ 60-80591

[51] Int. Cl.$^4$ ............................................. G01N 17/00
[52] U.S. Cl. ...................................... 73/865.6; 374/57
[58] Field of Search ........................... 73/865.6; 374/57

[56] References Cited

U.S. PATENT DOCUMENTS 4,544,995 10/1985 Suga ................................... 73/865.6

Primary Examiner—Tom Noland
Attorney, Agent, or Firm—Wenderoth, Lind & Ponack

[57] ABSTRACT

An optical deterioration-accelerating weather and optical resistance testing device has a light source and a frame supporting a sample to be tested rotating around the light source. Thermal deterioration of the sample due to radiant heat generated by the light source is inhibited by the provision of a cold air guide enclosing a portion of the sample rotating frame on which the sample is supported. Cold air is introduced to the surfaces of the sample through the cold air guide to maintain the both sides of the sample at a constant test temperature.

12 Claims, 3 Drawing Sheets

OPTICAL DETERIORATION-ACCELERATING WEATHER AND OPTICAL RESISTANCE TESTING APPARATUS

BACKGROUND OF THE INVENTION

1. Field of the Invention

This invention relates to an optical deterioration-accelerating weather and optical resistance testing apparatus for use in testing the weather and optical resistances of various kinds of materials and products while highly accelerating the optical deterioration thereof.

2. Description of the Prior Art

A prior art testing apparatus of this kind will now be described with reference to FIG. 2. FIG. 2 is a sectional side elevation view of a conventional optical deterioration-accelerating weather resistance testing apparatus according to Japanese Industrial Standards. Referring to the drawing, reference numeral 1 denotes a testing vessel provided with a light source 2 in the central portion thereof. A sample rotating frame 3 is rotated around the light source 2 by a rotary shaft 10 of the frame 3. A blower 8 circulates air introduced into the testing vessel via an air regulator 21 and a duct 22.

When the temperature in the vessel has reached a predetermined level, which is regulated by a temperature regulator, due to the heat generated from the light source 2, a valve 21a in the air regulator 21 is shifted to the position indicated by 21b. Consequently, outside air is introduced into the testing vessel 1, and hot air is discharged from an air discharge port 19, to cool the interior of the vessel. Namely, the valve 21a in the air regulator 21 is opened and closed in accordance with a temperature set by the temperature regulator, to switch the air flow passage.

A sample 4 receives the optical radiant energy from the light source 2, and the temperature of the sample increases due to the temperature in the testing vessel and the radiant energy, the sample 4 being deteriorated with the lapse of the test time. The distance between the light source 2 in the testing apparatus and the surface of the sample is 480 mm.

The testing temperature is measured with a black panel thermometer 9a (made by attaching a temperature measuring body close to a stainless steel plate of 150 mm in length, 70 mm in width and 1 mm in thickness, and coating the plate with black enamel) disposed adjacent the sample 4, and this temperature is suitably restricted.

An optical deterioration-accelerating weather and optical resistance testing apparatus is used to test the weather and optical resistance of various kinds of materials and products. The temperature and humidity of the air around and the quality of light applied to a sample constitute the important requisites for conducting tests and are required to be controlled stably for a long period of time.

In an optical deterioration-accelerating weather and optical resistance testing apparatus, a sample receives radiation from a light source, and the temperature of the sample thereby increases. For example, in a sunshine carbon arc light type optical deterioration-accelerating weather resistance testing apparatus, test conditions were determined as follows:

(a) Temperature of the surface of a sample measured with a black panel thermometer: 63°±3° C. or 83°±3° C.

(b) Illuminance of radiation of the surface of a sample: 255+45 w/m$^2$

However, regarding automobile parts, the optical deterioration-accelerating weather resistance tests have recently been conducted in more strict conformity with actual circumstances, i.e., the tests have been conducted at a temperature measured with a black panel thermometer of 80°–100° C. which is higher than a corresponding temperature used in similar tests before.

It has become necessary in recent years to require that materials and parts have a guaranteed life of 5–10 years, and, accordingly, the quality of materials has been improved year by year. The weather resistance of each material has also been very much improved. In conformity with such circumstances, as much as 1000 hours and not less than 2000 hours have recently been required in conducting tests for determining the weather resistance of material, whereas only about 500 hours were required before in conducting similar tests. In the current highly competitive technical world in which the testing techniques rapidly advance, a conventional testing apparatus of this kind cannot cope with the speed of development of materials and parts and the necessity to reduce test time for the determination of the weather resistance of the materials and parts.

Therefore, there has been a demand for a testing apparatus having excellent characteristics correlative with the outdoor exposure of a sample as in a conventional testing apparatus of this kind, and an optical deteriorating effect far superior to that of a conventional testing apparatus of this kind.

SUMMARY OF THE INVENTION

An object of the present invention is to meet the above-mentioned demand.

Another object of the present invention is to provide an optical deterioration-accelerating weather and optical resistance testing apparatus capable of increasing the radiant energy of the surface of a sample and thereby accelerating the optical deterioration of the sample to a greater extent than in a conventional testing apparatus of this kind.

Still another object of the present invention is to provide an optical deterioration-accelerating weather and optical resistance testing apparatus adapted to cool a sample with cold air applied to the rear and front surfaces thereof for the purpose of preventing the increased radiant energy from causing an increase in the temperature of sample, whereby the temperature of the sample can be regulated to a level which does not cause thermal deterioration of the sample which enables the test time to be greated reduced.

The present invention employs the following means to solve the problems previously mentioned.

An optical deterioration-accelerating weather and optical resistance testing apparatus according to the present invention has a testing vessel, a light source provided in the central portion of the testing vessel, a sample rotating frame adapted to be rotated about the light source, and a sample holder which has a sample supported thereon and which is attached to the sample rotating frame. The distance between the light source and the surface of the sample is small so as to increase the radiant energy on the surface of the sample thereby accelerating the optical deterioration of the sample. A cold air guide surrounds the rear surface of the sample and an air deflector is provided below the sample so as to prevent an excessive difference between the temperature of the front surface of the sample which is caused by such an increase in the radiant energy, and that of the rear surface thereof which causes thermal deterioration of the sample. The cold air is sent to the guide to cool the sample from the rear surface thereof. A plurality of air vents, the degree of opening of which can be regulated, are provided in the cylindrical air deflector disposed below the sample, to enable the cold air with which the rear surface of the sample has been cooled to be sent to the front surface thereof through the air vents.

When the light source, according to the present invention in which the distance between the light source the surface of the sample is approximately 1/5 of that in a conventional apparatus (for example, a case where such a distance is set in an embodiment of 210 mm as compared with that of 480 mm set in a conventional apparatus of this kind according to the Japanese Industrial Standards), is turned on, the amount of radiant energy on the surface of the sample increases in an inverse proportion to the square of the distance referred to above, and up to an amount atout 6 times as large as that in the conventional apparatus. Accordingly, the temperature of the surface of the sample, i.e. the temperature measured with the black panel thermometer, is not less than about 120° C.

As a result, the difference between the temperature of the front surface of the sample and that of the rear surface thereof would normally increase excessively as compared with that in a conventional testing apparatus of this kind, and the sample would be deteriorated due to such a temperature difference. This obstructs the achievement of the object of the invention of accelerating the optical deterioration of the sample. In order to eliminate this inconvenience, the increase in the temperature of the surface of the sample is prevented by the above-mentioned cooling process.

The above and other objects as well as advantageous features of the invention will become apparent from the following descriptions of the preferred embodiments taken in conjunction with the accompanying drawings.

DESCRIPTION OF THE PREFERRED EMBODIMENTS

The embodiments of the present invention will not be described with reference to the drawings.

Figure 1:
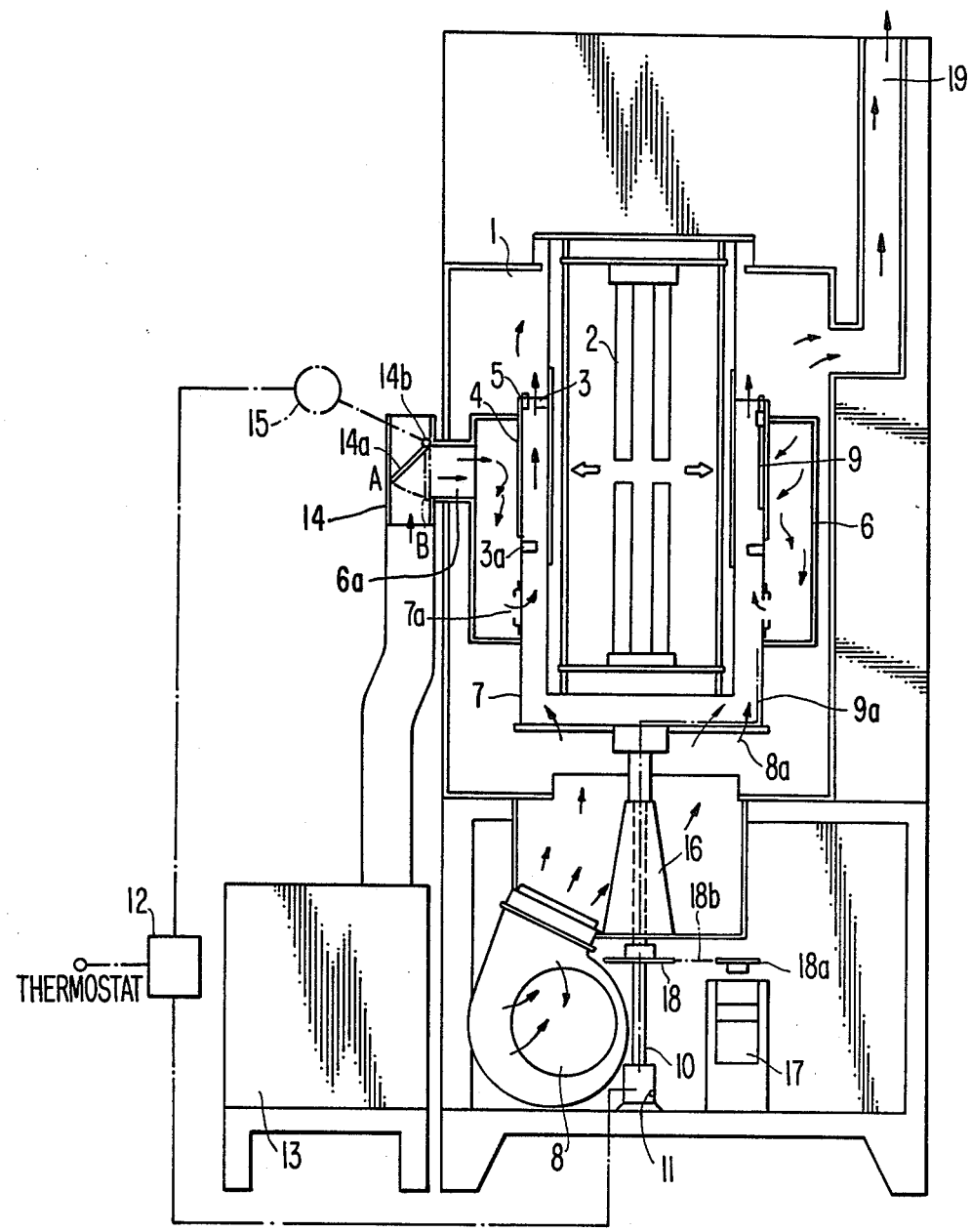
FIG. 1 is a sectional side elevation view of an embodiment of the present invention.
Figure 2:
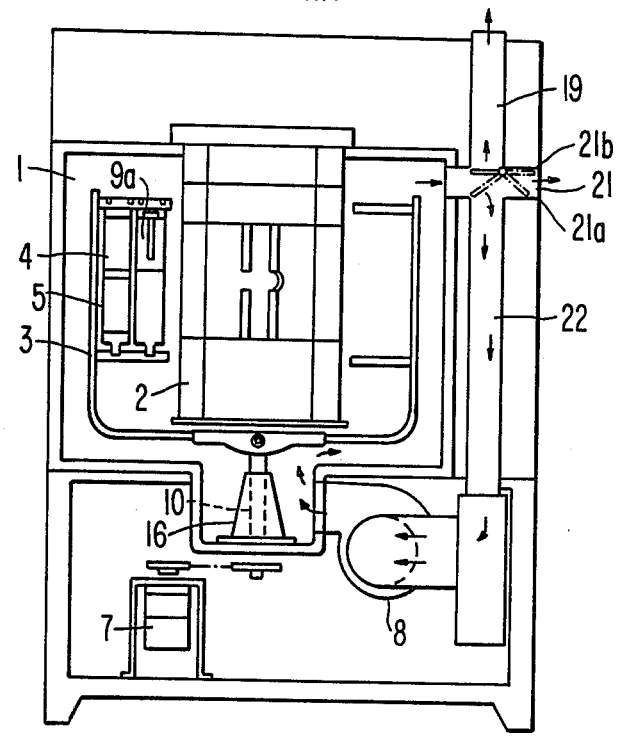
FIG. 2 is a sectional side elevation view of a prior art testing apparatus of this kind.

Referring to FIG. 1, reference numeral 1 denotes a testing vessel provided with a light source 2 in the central portion thereof, and a sample rotating frame 3 which is rotated about the light source 2 and has a sample holder 5 on which a sample 4 is supported. The sample 4 receives the radiant energy from the light source 2.

If the distance between the center of the light source 2 and the front surface of the sample 4 is less than that (480 mm) according to Japanese Industrial Standards in a conventional testing apparatus of this kind, the radiant energy on the surface of the sample increases inversely proportional to the square of this distance. According to the present invention, this distance is set, for example, at 210 mm.

Reference numeral 6 denotes a cold air guide surrounding the outer circumferential surface of the sample holder 5 so that a space is left between the outer surface of the sample holder 5 and the inner circumferential surface of the cold air guide 6. When cold air is sent from an air feed port 6a, the sample 4 is cooled therewith.

Figure 3A:
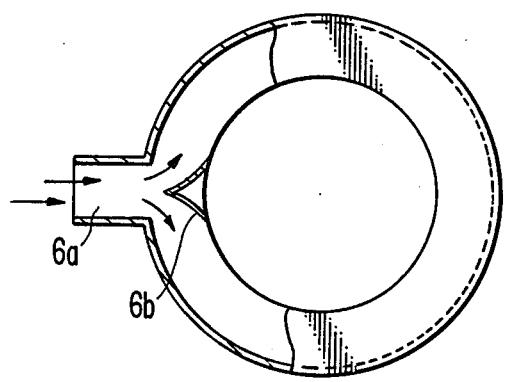
FIGS. 3(a) and 3(b)are a plan view and a section view respectively of a cold air guide according to the present invention.
Figure 3B:
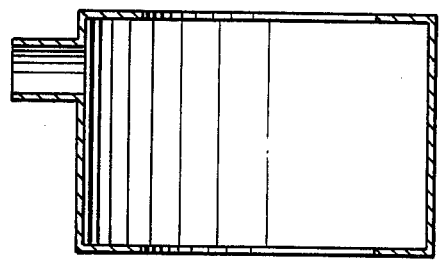

FIGS. 3(a) and 3(b) each show a schematic view of the cold air guide 6, in which reference numeral 6b denotes an air guide fixed to the air feed port 6a.

Again, referring to FIG. 1, reference numeral 7 denotes a cylindrical air deflector fixed to the lower portion of a lower ring 3a of the sample rotating frame 3 and having a plurality of air vents 7a in the circumferential wall thereof.

The cold air guide 6 mentioned above surrounds the air deflector 7 including the portion thereof which is provided with the air vents 7a. Accordingly, when the cold air is sent from the air feed port 6a, it cools the rear surface of the sample 4, and is then sent to the front surface thereof through the air vents 7a, so that the sample 4 is cooled effectively.

Figure 4:
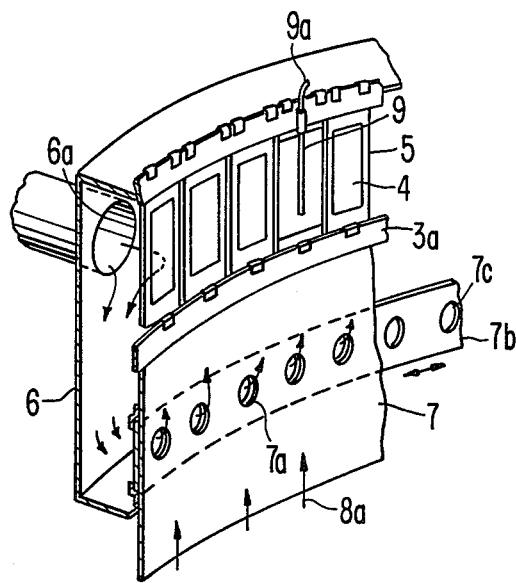
FIG. 4 is a perspective view showing a cold air guide, a sample rotating frame, a sample holder and an air deflector according to the present invention.

FIG. 4 is a perspective view showing the relation between the cold air guide 6, sample rotating frame 3, sample holder 5 and air deflector 7.

A slide ring 7b is fitted closely around the outer surface (or inner surface) of the air deflector 7, and air vents 7c, the number and pitch of which are equal to those of the air vents 7a in the air deflector 7, are provided in the circumferential wall of the slide ring 7b. If the air vents 7c and 7a are aligned with each other, they form completely-opened holes.

If the slider ring 7b is moved, the degree of opening of the air vents 7a can be regulated. This enables the flow rate of the cold air, which has been used to cool the rear surface of the sample 4, and which is then sent to the front surface thereof, to be regulated.

Reference numeral 8 denotes a blower for introducing outside air from the lower central portion of the testing vessel into the interior thereof. The air 8a introduced into the testing vessel 1 impinges upon the inner surface of the air deflector 7, and the greater part of the resultant air passes the front surface of the sample 4 and flows up toward the portion of the interior of the testing vessel 1 which is above the sample rotating frame 3. During this time, the flow of this air meets the cold air discharged from the air vents 7a, and is mixed therewith, the resultant mixture cooling the front surface of the sample 4.

Reference numeral 9 denotes a black panel temperature measuring member consisting of a platinum resistor of a thermoelectric material. The temperature of the temperature measuring member is regulated to a predetermined level and used as a test temperature. A lead wire 9a of the black panel temperature measuring member 9 extends through the interior of a hollow rotary shaft 10 of the sample rotating frame 3, and is connected to a slip ring (slide contact) 11. A fixed contact of the slip ring 11 is connected to a thermostat 12.

Reference numeral 13 denotes a cold air supply means, and the cold air therefrom is sent through a duct to the air feed port 6a via an air passage switching means 14. A shaft 14b fixed to one end of a valve 14a in the air passage switching means 14 is connected to a reversible motor 15, which is adapted to be driven by a signal from the thermostat 12.

The temperature of the black panel temperature measuring member 9 on the sample rotating frame 3 increases due to the radiation from the length source 2. In order to regulate this temperature to, for example, 83° C., the thermostat 12 is set to the same level.

When the temperature of the black panel temperature measuring member exceeds 83° C., the valve 14a assumes a position at A, and the cold air is introduced to the inside of the cold air guide 6. When the temperature of the black panel temperature measuring member has then dropped to 83° C. or lower, the reversible motor 15 is driven by a signal from the black panel temperature measuring member 9. Consequently, the valve 14a is shifted to assume a position at point B, and the cold air sent from the cold air supply means 13 does not enter the inside of the cold air guide 6 but is discharged directly to the outside air.

Reference numeral 16 denotes a bearing for the hollow rotary shaft 10; 17 denotes a motor for turning the sample rotating frame 3; 18 and 18a denote sprockets; 18b denotes a chain, and 19 denotes an air discharge port of the testing vessel.

The apparatus shown in FIGS. 1, 3 and 4 is an embodiment of the present invention. This embodiment is formed on the basis of a structure in which sample holders with samples supported thereon are attached to the upper and lower rings on the sample rotating frame, and a cooling mechanism is provided in this structure, in a similar manner as in a conventional apparatus of this kind.

In this embodiment, clearances are provided between the inner circumferential portions of the upper and lower flange-like annular plates of the cold air guide 6 and the outer circumferential surfaces of the sample holder 5 and air deflector 7 respectively so that the sample rotating frame 3, when rotating, is not caught by the inner circumferential portions of the cold air guide 6. In this arrangement, cold air escapes from the clearance which causes a cooling loss. The objects of the present invention can be achieved satisfactorily even by this embodiment. A structure capable of preventing such a cooling loss is shown in FIG. 5.

Figure 5:
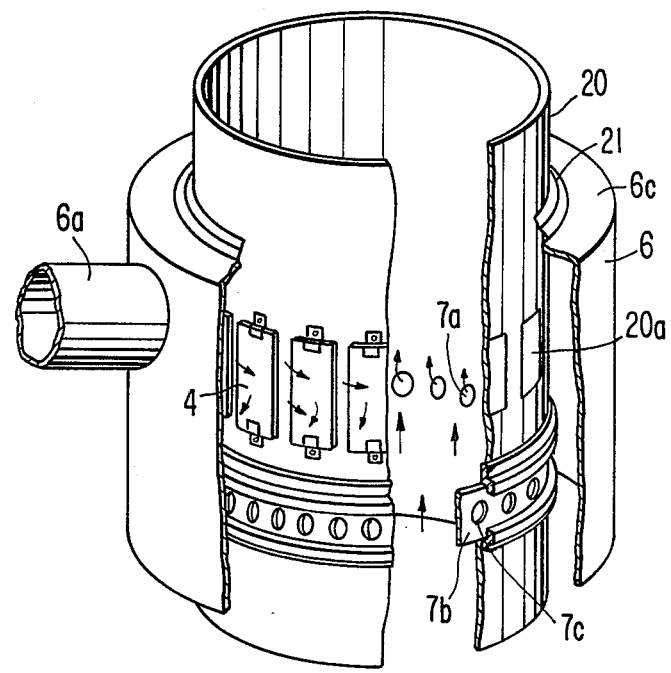
FIG. 5 is a perspective view of a cold air guide and a sample rotating drum of another embodiment of the present invention.

Referring to FIG. 5, reference numeral 20 denotes a rotary drum which is a unitary combination of the above-mentioned sample rotating frame 3, sample holder 5 and air deflector 7, and which is adapted to be rotate about the light source 2.

The rotary drum 20 is provided with exposure windows 20a, and samples 4 are applied to the rotary drum 20 on the outer side of these exposure windows 20a and fastened thereto. The circumferential portion of the rotary drum 20 which is below the exposure windows 20a is provided with air vents 7a. A slide ring 7b having air vents 7c is fitted around the air vents 7a, so that the degree of opening of the air vents 7a can be regulated in the same manner as in the above-described embodiment.

Reference numeral 6 denotes a cold air guide, and 6a denotes an air feed port. The inner circumferential portions of the upper and lower flange-like annular plates 6c of the cold air guide 6 are spaced slightly from the outer circumferential portion of the rotary drum 20. If, for example, rubber ring seals 21 having L-shaped cross-sections are fixed to the flange-like annular plates 6c so that the inner circumferential portions of the ring seals 21 are joined firmly to the corresponding outer circumferential portions of the rotary drum 20, the portions of the inside of the cold air guide 6 which are in the vicinity of the ring seal-attached to the outer circumferential portions of the rotary drum 20, are sealed completely.

When the cold air is sent from the air feed port 6a, it cools the samples 4 from the rear surfaces thereof without any cooling loss, and is then sent to the front surfaces of the samples 4 through the air vents 7a, 7c.

A conventional apparatus of this kind and an apparatus according to the present invention were compared and comparative results with respect to the quality of radiant energy are shown in Table 1, with respect to the blue scale test time are shown in Table 2, and with respect to the time of testing films of coating materials are shown in Table 3.

TABLE 1

| | RADIANT ENERGY | | |
|---|---|---|---|
| Wavelength range | Conventional apparatus | Apparatus according to the present invention | Ratio (present invention/ prior art) |
| Ultraviolet visible portion 300–700/nm | 255 w/m$^2$ | 1496 w/m$^2$ | 5.9 |

TABLE 2

| Blue Scale grade | Test time required by conventional apparatus | Test time required by an apparatus according to the present invention to obtain a color difference in the test conducted by using the conventional apparatus | Ratio of acceleration of optical deterioration Test time required by a conventional apparatus/ Test time required by an apparatus according to the present invention |
|---|---|---|---|
| Third Grade | 9 hours | 0.95 hours | 9.5 |
| Fourth Grade | 20 hours | 1.9 hours | 10.5 |

TABLE 3

| Kinds of films of coating materials | | Test time required by a conventional apparatus (temperature measured with a black panel temperature measuring member regulated for 63° C.) | Test time required by an apparatus according to the present invention to obtain a color difference identified with that obtained in the test conducted by using the conventional apparatus (temperature measured with a black panel temperature measuring member regulated for 83° C.) | Ratio of acceleration of optical deterioration. Test time required by a conventional apparatus/Test time required by an apparatus according to the present invention |
|---|---|---|---|---|
| Kind. of resins | Colors | | | |
| Amino alkyd resin | Red Blue Yellow | 720 hours on an average | 58.3 hours on an average | 13.6 on an average |
| Thermosetting acrylic resin | Red Blue Yellow | 720 hours on an average | 57.5 hours on an average | 13.1 on an average |
| Acrylic lacquer | Red Blue Yellow | 720 hours on an average | 47.5 hours on an average | 15.2 on an average |
| Acrylic urethane | Red Blue Yellow | 720 hours on an average | 69.3 hours on an average | 10.4 on an average |
| Average: | | 720 hours | 59.1 hours | 13.1 |

The results of the tests show that the apparatus according to the present invention is capable of conducting tests at such an optical deterioration acceleration rate that is as about 10-15 times as high as that of the rates at which similar tests are conducted by using a conventional apparatus of this kind. Namely, a test, which requires, for example, 1000 hours to be carried out by using a conventional apparatus of this kind, can be carried out in only 70-100 hours by using an apparatus according to the present invention.

Since the present invention is constructed as described above, the radiant energy on the surface of a sample can be increased to about 6 times of that in a conventional apparatus of this kind, and an increase, which occurs due to this increase in the quantity of radiant energy, in the temperature of the sample is suppressed by the above-mentioned cooling mechanism so as to prevent the sample from being thermally deteriorated. Therefore, the present invention enables the time, which is required by a conventional optical deterioration-accelerating weather resistance testing apparatus to conduct a test, to be reduced greatly to 1/10-1/15 of that required by the conventional testing apparatus. Thus, the present invention achieves an expedition of the development and research of materials and products, the reduction of test time and a labor-saving and energy-saving advantage in the testing apparatus.

The present invention is not, of course, limited to the above embodiments; it may be modified in various ways within the scope of the appended claims.

What is claimed is:

1. An optical deterioration-accelerating weather and optical resistance testing apparatus for testing the weather and optical resistance of a sample, said apparatus comprising:
    a testing vessel;
    a light source within said vessel at a central portion thereof;
    a sample rotating frame disposed around said light source and rotatably mounted within said vessel for rotating about said light source, said sample rotating frame having a plurality of air vents extending therethrough;
    adjusting means for adjusting the degree of opening of said plurality of air vents extending through said sample rotating frame,
    a sample holder attached to said sample rotating frame and spaced from said plurality of air vents, said sample holder securing the sample to said sample rotating frame for exposing a front surface of the sample to said light source;
    a cold air guide within said testing vessel and disposed around said sample rotating frame so as to enclose said sample holder therein, a rear surface of the sample attached to said sample holder exposed within said cold air guide; and
    cold air supply means connected to said cold air guide for introducing cold air into said cold air guide which first cools the rear surface of the sample, passes through said plurality of air vents and then cools the front surface of the sample thereby inhibiting thermal deterioration of the sample by radiant heat generated by said light source during optical resistance testing of the sample.

2. An optical deterioration-accelerating weather and optical resistance testing apparatus as claimed in claim 1,
    wherein said cold air supply means includes a switching means for selectively introducing the cold air to said cold air guide; and further comprising
    a temperature measuring means attached to said sample rotating frame adjacent said sample holder and the front surface of the sample when the sample is secured to said sample rotating frame by said sample holder, said temperature measuring means measuring the approximate temperature of the sample exposed to said light source; and
    a thermostat operatively connected between said temperature measuring means and said switching means for regulating the temperature at which the sample is to be tested, said thermostat actuating said switching means to allow cold air to be introduced from said cold air supply means to said cold air guide when the temperature measured by said temperature measuring means is below a predetermined test temperature for the sample, and said theremostat actuating said switching means to stop cold air from being introduced by said cold air supply means to said cold air guide when the temperature measured by said temperature measuring means is above said predetermined test temperature.

3. An optical deterioration-accelerating weather and optical resistance testing apparatus as claimed in claim 2, wherein said sample rotating frame has at least one exposure window extending therethrough above said plurality of air vents and in which the sample is secured by said sample holder.

4. An optical deterioration-accelerating weather and optical resistance testing apparatus as claimed in claim 3, wherein said cold air guide comprises a cylindrical body radially spaced around said sample rotating frame, a first annular flange extending from one end of said cylindrical body toward said sample rotating frame and spaced slightly radially therefrom, a second annular flange extending from the other end of said cylindrical body toward said sample rotating frame and spaced slightly radially therefrom, and a respective rubber ring seal attached to each of said first and said second annular flanges and extending therefrom against said sample rotating frame for sealing the respective radial spaces between said flanges and said sample rotating frame, each of said rubber ring seal having an L-shaped cross-section.

5. An optical deterioration-accelerating weather and optical resistance testing apparatus as claimed in claim 2, wherein said cold air guide comprises a cylindrical body radially spaced around said sample rotating frame, a first annular flange extending from one end of said cylindrical body toward said sample rotating frame and spaced slightly radially therefrom, a second annular flange extending from the other end of said cylindrical body toward said sample rotating frame and spaced slightly radially therefrom, and a respective rubber ring seal attached to each of said first and said second annular flanges and extending therefrom against said sample said sample rotating frame for sealing the respective radial spaces between said flanges and said sample rotating frame, each of said rubber ring seal having an L-shaped cross-section.

6. An optical deterioration-accelerating weather and optical resistance testing apparatus as claimed in claim 1, wherein the distance between said light source and the sample rotating frame disposed around said light source is approximately 210 mm.

7. An optical deterioration-accelerating weather and optical resistance testing apparatus as claimed in claim 1, wherein said cold air guide is radially spaced from said sample rotating frame so as to define a slight radial clearance between said cold air guide and the outer periphery of said sample rotating frame.

8. An optical deterioration-accelerating weather and optical resistance testing apparatus as claimed in claim 1, wherein said cold air guide has an air feed port connected to said cold air supply means and an air guide plate adjacent said air feed port for deflecting cold air introduced into said air feed port by said cold air supply means to both sides of said air feed port and around said cold air guide.

9. An optical deterioration-accelerating weather and optical resistance testing apparatus as claimed in claim 1, wherein said sample rotating frame comprises an upper portion to which said sample holder is attached, a lower ring extending around the bottom of said upper portion, and a cylindrical air deflector attached to said lower ring and through which said plurality of air vents extend.

10. An optical deterioration-accelerating weather and optical resistance testing apparatus as claimed in claim 9, wherein said cold air guide is disposed around said sample rotating frame so as to enclose said plurality of air vents therein.

11. An optical deterioration-accelerating weather and optical resistance testing apparatus as claimed in claim 10, wherein said adjusting means comprises a slide ring slidably attached around said sample rotating frame over said plurality of air vents, said slide ring having a plurality of air holes extending therethrough at positions corresponding to the positions at which said air vents extend through said sample rotating frame.

12. An optical deterioration-accelerating weather and optical resistance testing apparatus as claimed in claim 1, and further comprising an auxiliary air blower for suppling cold air into said sample rotating frame to mix with the cold air introduced into said cold air guide that has passed through said plurality of air vents prior to cooling the front surface of the sample.

* * * * *